United States Patent

Naganuma et al.

Patent Number: 6,126,644
Date of Patent: Oct. 3, 2000

[54] HOLDER FOR A SYRINGE AND AN INJECTION DEVICE USING THE HOLDER

[75] Inventors: Masateru Naganuma, Kanagawa; Yoshihisa Itoh, Tokyo, both of Japan

[73] Assignees: Seikagaku Kogyo Kabushiki Kaisha; Top Corporation, both of Tokyo, Japan

[21] Appl. No.: 08/980,868

[22] Filed: Dec. 1, 1997

[30] Foreign Application Priority Data

Nov. 29, 1996 [JP] Japan .................................. 8-335011

[51] Int. Cl.⁷ .................................................. A61M 5/00
[52] U.S. Cl. .......................... 604/232; 604/187; 604/241
[58] Field of Search .................................. 604/191, 192, 604/220, 187, 227, 228, 232, 234, 240, 241

[56] References Cited

U.S. PATENT DOCUMENTS

| | | | |
|---|---|---|---|
| 3,101,084 | 8/1963 | Hamilton | 128/218 |
| 3,223,282 | 12/1965 | Kloehn | 222/41 |
| 3,958,570 | 5/1976 | Vogelman et al. | 128/218 DA |

FOREIGN PATENT DOCUMENTS

| | | | |
|---|---|---|---|
| 57-100935 | 6/1982 | Japan | A61M 5/31 |
| 62-144666 | 6/1987 | Japan | A61M 5/18 |
| 21289 | 1/1990 | Japan | A61M 5/178 |
| 648679 | 7/1994 | Japan | A61M 5/31 |
| 731679 | 2/1995 | Japan | A61M 5/31 |
| WO 94/13347 | 6/1994 | WIPO | A61M 5/32 |

*Primary Examiner*—Ronald Stright
*Assistant Examiner*—Michael J. Hayer
*Attorney, Agent, or Firm*—Sughrue, Mion, Zinn, Macpeak & Seas, PLLC

[57] ABSTRACT

A holder has an inner diameter which allows the holder to be fitted onto the outside of a cylinder barrel 2 and is formed into a tubular shape having a length which is substantially equal to that of the cylinder barrel 2. The holder has a flange 73 at the basal end.

27 Claims, 5 Drawing Sheets

HOLDER FOR A SYRINGE AND AN INJECTION DEVICE USING THE HOLDER

BACKGROUND OF THE INVENTION

The invention relates to a holder for a syringe, particularly to a holder to be attached to a syringe which is used for injecting liquid or gel and which has a cylinder barrel of a relatively small diameter and made of glass, and also to an injection device using the holder.

Conventionally, the length and diameter of a syringe are determined in accordance with the amount and kind of liquid or gel to be injected, in a range wherein the syringe can be easily operated.

However, a syringe which is used for injecting a small amount of liquid or gel is short in length in the longitudinal direction thereof and has a small diameter. Therefore, such a syringe hardly fits in the hand and is poor in operability. This defect of the syringe causes a problem when the syringe is used in a case where delicate operations are required, such as in the case of an ophthalmic operation.

Recently, a cylinder barrel which constitutes a syringe is often made of a synthetic resin. Depending on the kind of the charged parenteral solution, however, a cylinder barrel must be made of glass. Many syringes in the form of an ampule into which a predetermined amount of liquid or gel is previously charged (so called as a pre-filled syringe) are recently used. In such a pre-filled syringe, a cylinder barrel made of glass is used in order to prevent the quality of the liquid or gel from being deteriorated during the preservation period.

Unlike a syringe made of a synthetic resin, in a cylinder barrel made of glass, it is difficult to increase the size of a finger holding portion because of restrictions caused by characteristics of glass and a manufacturing process and so on.

When the piston is pressed so as to eject the liquid or gel, therefore, only a part of a finger is held by the finger holding portion, so that stable ejection is hardly conducted. This is noticeable particularly in the case where liquid or gel of high viscosity such as a hyaluronic acid preparation or a solution of hydroxypropyl methylcellulose is used.

To comply with this, as disclosed in, for example, Japanese utility model unexamined publication (Kokai) No. Sho. 57-100935 discloses a structure in which a holder having a flange of a large diameter is fitted onto a cylinder barrel so as to practically increase the size of a finger holding portion.

Since the holder disclosed in the publication is intended only to improve the finger holding portion, the holder has the maximum length which is approximately equal to the width of a finger and is fitted to the basal end of the cylinder barrel, and a stepped portion is formed between the cylinder barrel and the holder. Therefore, the holder has a problem in that a syringe cannot be operated under a stable state in the case such as the holding of the syringe or the insertion of the needle.

On the other hand, a glass cylinder barrel is used while an injection needle is fittingly inserted under a pressure into and supported by a fitting part of a neck portion formed at the tip end of the cylinder barrel. In the case where liquid or gel of high viscosity is to be injected into the object, for example, a high pressure of the liquid or gel is applied to the injection needle. When the press insertion is not sufficient, there is a fear that the applied high pressure may cause the injection needle to slip off.

SUMMARY OF THE INVENTION

The invention has been conducted in view of the circumstances. It is an object of the present invention to improve the finger holding property during the use of a syringe, to allow a syringe to be operated in a stable state in the case such as the holding of the syringe or the insertion of the needle, and to eliminate a fear that the injection needle may slip off during a process of injecting liquid or gel.

The above-mentioned object can be attained by a holder for a syringe, according to the present invention, having a piston and a cylinder barrel in which a neck portion for attaching an injection needle is formed at a tip end of the cylinder barrel and the piston is fittingly inserted into the cylinder barrel through an opening formed at a basal end portion thereof, wherein the holder is formed into a tubular shape having an inner diameter which allows the holder to be fitted onto an outside of the cylinder barrel of the syringe, and a length which is substantially equal to a length of the cylinder barrel, and the holder is formed at a basal end thereof with a flange.

With the holder according to the invention, a substantially whole portion of the cylinder barrel is covered by the holder having an outer diameter which is larger than that of the cylinder barrel of the syringe and is uniformly extended in the axial direction of the syringe, so that the syringe can be used under a stable state by gripping the holder having the uniformed larger diameter.

Furthermore, in the case where a pre-filled syringe is of a medicated syringe, it is preferable to modify the above-mentioned construction according to the present invention into a construction that a cap is fitted to the neck portion, and the piston is fittingly inserted in the cylinder barrel by a predetermined distance from the opening in such a manner that a predetermined amount of liquid or gel is charged into the cylinder barrel. Therefore, damage is prevented from occurring during storage, transportation, and the like.

In the above-mentioned construction of the invention, a locking mechanism portion for an injection needle, such as a luer lock mechanism may be formed at the tip end of the holder. Consequently, an injection needle attached to the neck portion of the cylinder barrel constituting the syringe is fixed to the holder. Even when a high pressure is applied to the needle during injection of a liquid medicine of high viscosity such as a hyaluronic acid preparation or a solution of hydroxypropyl methylcellulose, or a gel-like medicine, or when the cylinder barrel is broken, there is no fear that the injection needle slips off. The locking mechanism portion for an injection needle is not restricted to a luer lock mechanism formed at the tip end and may be configured by another structure. The locking mechanism portion may be formed on either of the inner and outer sides of the tip end of the holder.

In the above-mentioned construction according to the present invention, furthermore, the cylinder barrel constituting the syringe and the holder may be completely integrated by a fixing member which is disposed under a state where a piston rod is passed through the member, and which is fixed to the end face of the flange on the side of the basal end with interposing the basal end of the cylinder barrel between the flange and the fixing member. Therefore, the operability can be further enhanced.

Moreover, the fixing member and the flange may be fixed to each other via a fixing mechanism, thereby enabling the fixing member and the flange to be fixed to each other without producing relative backlash or rotation.

In addition, the above-mentioned object can be attained by an injection device according to the present invention comprising, a syringe having a piston and a cylinder barrel in which a neck portion for attaching an injection needle is formed at a tip end of the cylinder barrel and the piston is fittingly inserted into the cylinder barrel through an opening formed at a basal end flange portion thereof, a holder formed into a tubular shape having an inner diameter which allows the holder to be fitted onto an outside of the cylinder barrel of the syringe, wherein a length of said holder which is substantially equal to a length of the cylinder barrel, and the holder is formed at a basal end thereof with a flange.

In the above-mentioned injection device according to the present invention, a cap may be fitted to the neck portion, and the piston may be fittingly inserted in the cylinder barrel by a predetermined distance from the opening in such a manner that a predetermined amount of liquid or gel is charged into the cylinder barrel.

In addition, in the above-mentioned injection device, liquid or gel may be medicine and the medicine may be a liquid medicine of high viscosity or a gel-like medicine.

Further, in the above-mentioned injection device, the medicine may be a hyaluronic acid preparation.

The above-mentioned object can also be attained by a holder for syringe according to the present invention including a cylinder barrel made of a glass and having at a tip end a neck portion for attaching an injection needle and at a basal end a flange portion, and a piston fittingly inserted into the cylinder barrel through an opening formed at the flange portion, wherein the tubular shaped holder comprises:

a holder made having a tubular shaped holder body made of a hard synthetic resin an inner diameter of which allows the holder to be fitted onto an outside of the cylinder barrel of the syringe, and a length of which is substantially equal to a length of the cylinder barrel, and the holder body being provided at a basal end thereof with a flange which is brought in engagement with the flange portion of the cylinder barrel.

The above-mentioned holder for a syringe according to the present invention, may further comprise:

a locking mechanism provided at a tip end of the holder body for lockingly attaching the injection needle to the holder body and the syringe at the neck portion.

In the above-mentioned holder for a syringe according to the present invention, the piston may be fittingly inserted into the cylinder barrel by a predetermined distance from the opening of the flange portion in such a manner that a predetermined amount of liquid or gel is charged into the cylinder barrel.

In addition, the above-mentioned holder for a syringe according to the present invention, may further comprise;

a fixing member for fixing the flange portion of the cylinder barrel to the flange of the holder body so as to prevent the syringe from being moved relative to the holder in an axial direction of the syringe.

Further, in the above-mentioned holder for a syringe according to the present invention, may further comprise:

a fixing mechanism for fixing the flange portion of the cylinder barrel to the flange of the holder body so as to prevent the syringe from being moved relative to the holder in a rotational direction of the syringe.

Furthermore, in the above-mentioned construction, the fixing mechanism may comprise:

a reception seat made of a soft material for fittingly receiving the basal end flange portion of the cylinder barrel; and a recessed portion formed in a basal end face of the flange for receiving the reception seat.

The above-mentioned object can also be attained by an injection device, according to the present invention, which comprises:

a syringe including,
a cylinder barrel made of a glass and having at a tip end a neck portion for attaching an injection needle and at a basal end a flange portion, and
a piston fittingly inserted into the cylinder barrel through an opening formed at the flange portion; and a holder having a tubular shaped holder body made of a hard synthetic resin, an inner diameter of which allows the holder to be fitted onto an outside of the cylinder barrel of the syringe, and a length of which is substantially equal to a length of the cylinder barrel, and the holder body being provided at a basal end thereof with a flange which is brought in engagement with the flange portion of the cylinder barrel.

In addition, in the above-mentioned injection device, the piston may be fittingly inserted into the cylinder barrel by a predetermined distance from the opening in such a manner that a predetermined amount of liquid or gel is charged into the cylinder barrel.

DETAILED DESCRIPTION OF THE PREFERRED EMBODIMENTS

Hereinafter, preferable embodiments according to the present invention will be described.

Figure 1:
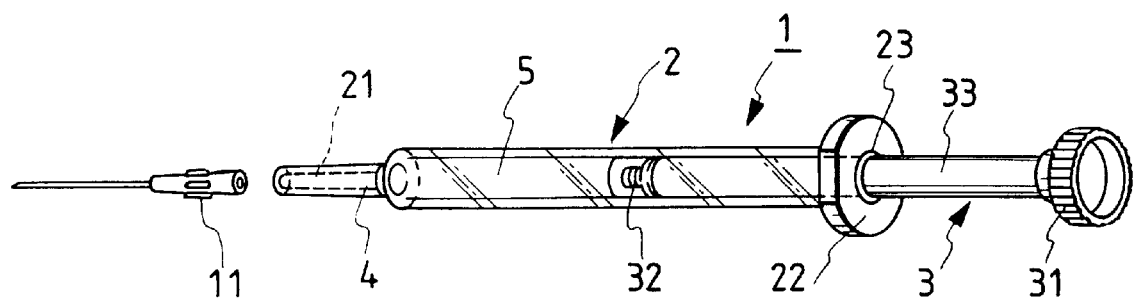
FIG. 1 is an exploded perspective view showing a syringe.

The accompanying drawings show one of preferred embodiments in which the invention is applied to a so-called pre-filled syringe. As shown in FIG. 1, in the used syringe 1, a piston 3 in which a gasket 32 is fixed to the tip end of a piston rod 33 is fittingly inserted into a glass cylinder barrel 2 which has a neck portion 21 for attaching an injection needle at a tip end, and which has also a basal end portion 22, from the side of the basal end opening 23 of the cylinder barrel. A cap 4 is attached to the neck portion 21. The piston 3 is fittingly inserted to a predetermined position so that a predetermined amount of a medicine 5 is charged into the cylinder barrel 2.

Figure 2:
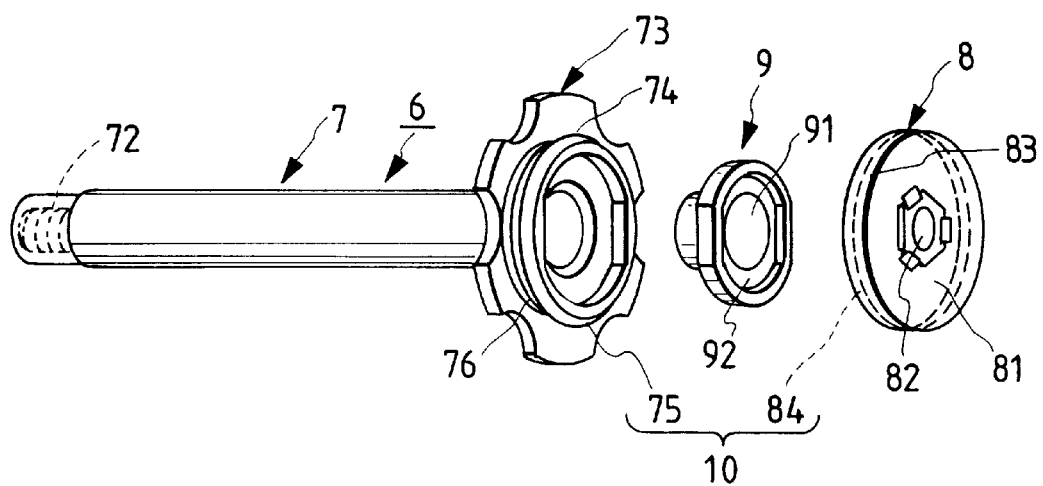
FIG. 2 is an exploded perspective view showing a holder according to the preferred embodiment of the invention.

As shown in FIG. 2, a holder 6 according to the invention comprises the holder body 7 which is formed into a tubular shape, a fixing member 8 which is used for fixing the holder body 7 to the cylinder barrel 2, and a reception seat 9 which prevents backlash between the holder 6 and the cylinder barrel 2 from occurring and which is made of a soft material such as synthetic rubber.

Figure 4:
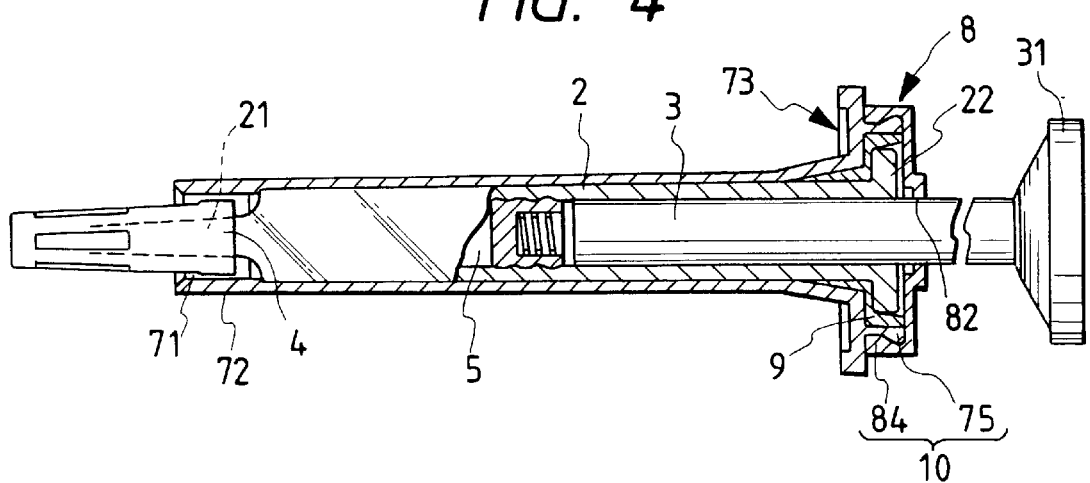
FIG. 4 is a partially cutaway enlarged section view taken along the line A—A of FIG. 3.

The holder body 7 is made of a hard synthetic resin such as polystyrene, and has an inner diameter which allows the holder 6 to be fitted onto the outside of the cylinder barrel 2, and a length which is substantially equal to that of the cylinder barrel 2. As shown in FIGS. 2 and 4, locking mechanism portion 72 for an injection needle and configured by a spiral ridge is formed on the inner peripheral face 71 of the tip end of the holder body. A flange 73 is formed at the basal end of the holder body. The flange 73 is wider than the basal end flange portion 22 configured by a finger holding projection which is formed on the cylinder barrel 2 of the syringe 1. A cylindrical engaging member 76 is integrally molded on the end face 74 on the side of the basal end of the flange 73. The engaging member 76 has a size and a height which allow the basal end flange portion 22 and the reception seat 9 which will be described later, to be buried in the engaging member 76. A first annular engaging ridge 75 is projected along the outer peripheral face of the peripheral wall of the engaging member 76 so as to define a recessed portion for accommodating the basal end flange portion 22 together with the reception seat 9 therein.

The fixing member 8 is a shallow bottomed cylinder which is to be fitted onto the outer peripheral face of the cylindrical engaging member 76 that is projected on the end face 74 on the side of the basal end of the flange 73. The fixing member 8 is made of, for example, hard polypropyrene resin. A through hole 82 for the piston rod 33 of the syringe 1 to be inserted is formed at the center of a disk portion 81. A second annular engaging ridge 84 is projected on the inner peripheral face of a cylinder portion 83 so as to elongate along the open end. The second annular engaging ridge is fitted to the first annular engaging ridge 75. The second engaging ridge 84, and the first engaging ridge 75 formed on the flange 73 constitute a fixing mechanism 10.

As shown in FIG. 2, the reception seat 9 is formed into a shape which allows the seat to be fitted into the cylindrical engaging member 76 formed on the end face 74 on the side of the basal end of the flange 73, and made of a suitable soft material such as an olefin elastomer. A fitting insertion hole 91 for the cylinder barrel 2 of the syringe 1 is formed at the center of the reception seat. A fitting insertion groove 92 into which the basal end flange portion 22 of the cylinder barrel 2 is embedded is formed in the end face on the side of the basal end of the receptor seat so as to be continuous with the fitting insertion hole 91.

Figure 3:
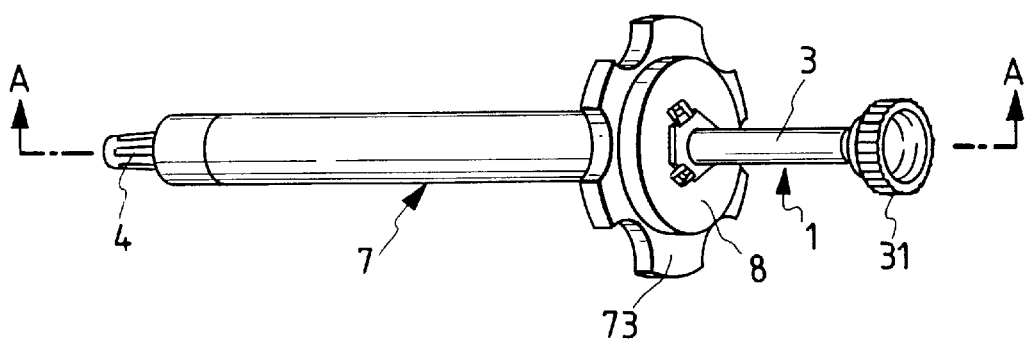
FIG. 3 is a perspective view showing an assembled state of the embodiment of the holder shown in FIG. 1 with syringe shown in FIG. 1.

The thus configured embodiment is formed as a product of an injection device of the present invention as shown in FIGS. 3 and 4 in a state wherein, the piston rod 33 is previously passed through the fixing member 8, the cylinder barrel 2 of the syringe 1 is then inserted through the reception seat 9 into the holder body 7 from the basal end of the holder body 7 until the tip end face of the fixing member 8 abuts against the flange 73 as shown in FIG. 4, and the fixing member 8 is advanced toward the flange 73 and fitted onto the outside of the engaging member 76 as shown in FIG. 4. In this assembled state shown in FIGS. 3 and 4, the injection device using the holder is shipped off, as a product on the market.

At this time, the first engaging ridge 75 and the second engaging ridge 84 which constitute the fixing mechanism 10 are fitted to each other. Therefore, the basal end flange portion 22 of the cylinder barrel 2 is clamped between the fixing member 8 and the end face 74 on the side of the basal end of the flange 73, whereby the holder 6 and the basal end flange portion 22 are surely fixed to each other.

Figure 5:
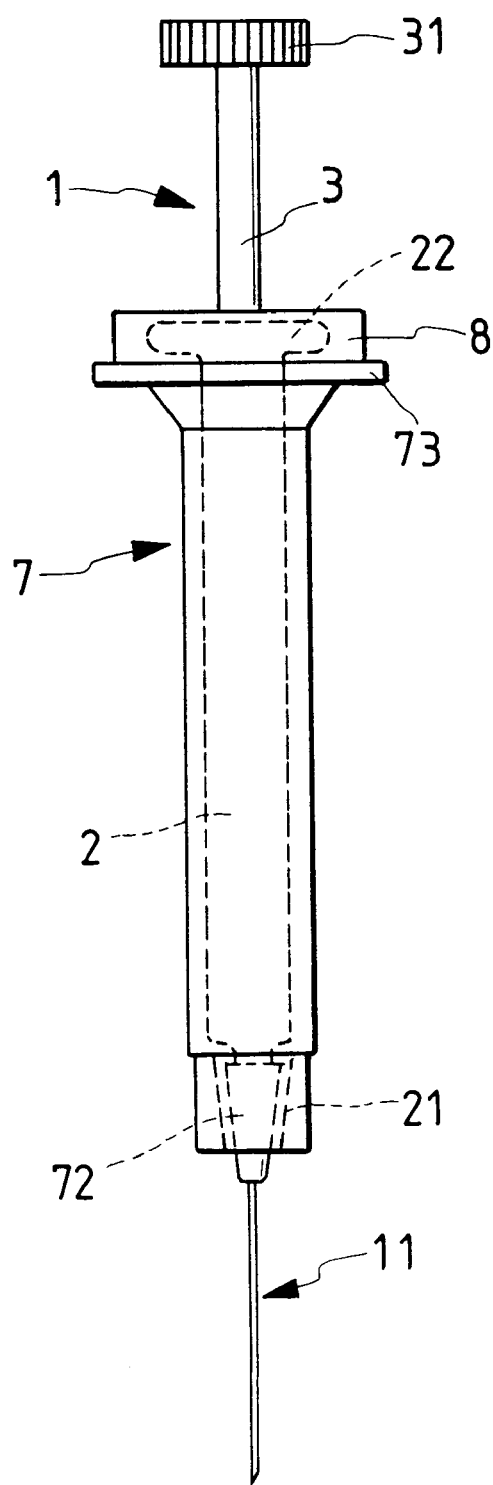
FIG. 5 is a front view showing a use state of the embodiment shown in FIG. 3.

The syringe 1 which is attached to the holder 6 according to the embodiment is used in the following manner (not shown). An injection needle 11 is attached to the neck portion 21 from which the cap 4 is detached as shown in FIG. 5, the holder 6 is caught by the index and middle fingers in the same manner as a prior art syringe, and a pressing portion 31 which is disposed at the tip end of the piston rod 33 is then pushed or pulled by the thumb. Since a substantially whole portion of the cylinder barrel 2 is covered by the holder 6 of the invention, the whole of the cylinder barrel 2 has the same diameter which is enlarged, and hence the syringe can be used under a stable state.

Particularly, since the clamping fixation of the basal end flange portion 22 by the fixing member 8 fixed to the flange 73 and the end face 74 on the side of the basal end of the flange 73 enables the holder 6 and the basal end flange portion 22 to be surely fixed to each other, the holder 6 and the cylinder barrel 2 are integrated with each other. The resulting structure is very easy to handle, and there is no fear that the holder 6 slips off.

The injection needle 11 is lockingly attached to the locking mechanism portion 72 for the injection needle 11 which is formed on the inner side of the tip end of the holder body 7 in turn to the neck portion 21 of the cylinder barrel 2. In this embodiment, a luer locking mechanism is applied to the locking mechanism portion 72.

Figure 8:
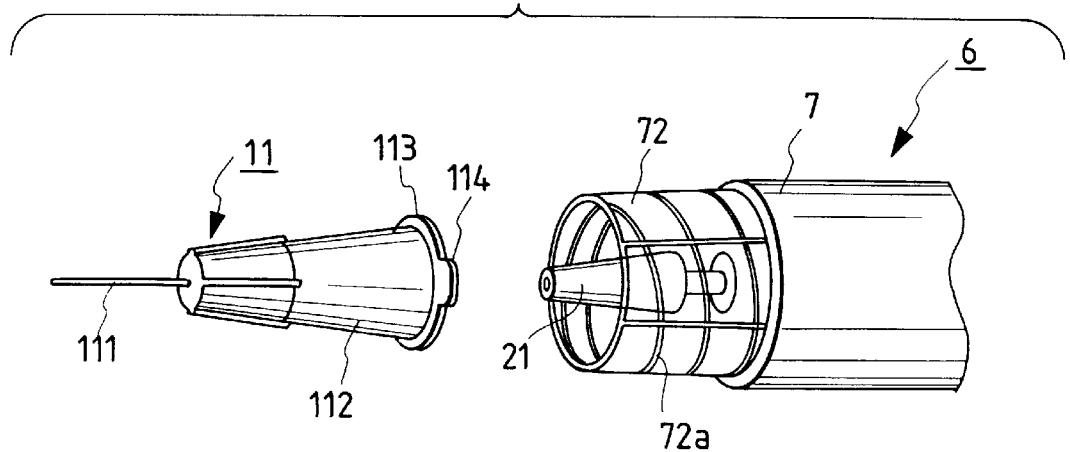
FIG. 8 is a perspective view showing a luer locking mechanism in a disassembled state which applicable to a locking mechanism portion according to the present invention.
Figure 9:
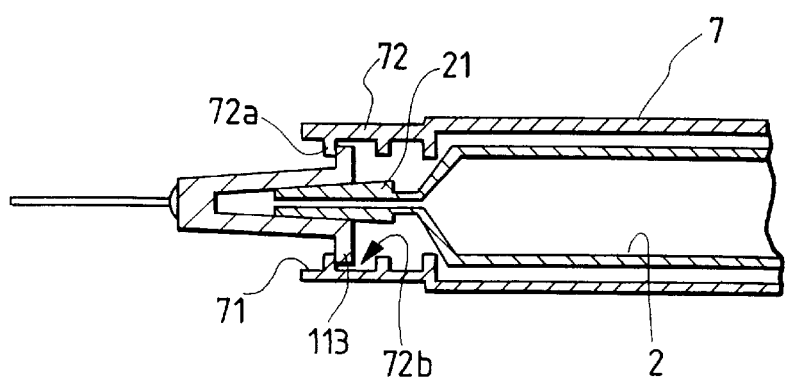
FIG. 9 is a cross-sectional view showing the luer locking mechanism in an assembled state shown in FIG. 8.

Note that the luer locking mechanism is well-known as a mechanism for fixing an injection needle to a syringe, and is for example standardized in American National Standard ANSI/HIMA MD70.1-1983. As shown in FIGS. 8 and 9, the luer locking mechanism is defined by a combination between a flange 113 with a lug 114 and a spiral ridge 72a. The lug 114 is outwardly protruded in a radial direction from a flange 113 formed at a basal tip end of a needle base portion 112 to which a needle body 111 is attached. The spiral ridge 72a, which is inwardly protruded in the radial direction, is formed on the inner peripheral surface 71 of the holder body 7. The injection needle 11 is securely fixed to the holder body 7 as follows. The needle base portion 112 of the injection needle 11 is inserted into the tip end of the holder body 7 by rotating the injection needle 11 relative to the holder body 7 while the lug 114 is being slid into a groove 72b defined between the spiral ridges 72a and guided along the spiral ridge 72a. As a result of this, the flange 113 with the lug 114 of the needle base portion 112 is threadedly engaged with the locking mechanism portion 72 of the holder body 7. Accordingly, the injection needle 11 is securely fixed to the holder 6.

This configuration eliminates the fear that the injection needle 11 slips off in cases such as that a high pressure is applied to the needle, for example, when liquid or gel of high viscosity is injected, or when the cylinder barrel 2 is broken.

The configuration in which the reception seat 9 for the basal end flange portion 22 and made of a soft material is disposed on the end face 74 on the basal end side of the flange 73 allows the basal end flange portion 22 of the cylinder barrel 2 to be fixed to the flange 73 without producing backlash.

In the embodiment, particularly, the inner face of the engaging member 76 formed into a shape which can fit with the basal end flange portion 22 of the sylinge, and then the basal end flange portion 22 and the engaging member 76 are fitted to each other with interposing the reception seat 9 therebetween, whereby rotation and backlash between the holder body 7 and the syringe 1 are prevented from occurring. Therefore, the syringe can be easily operated in a case such as that the cap 4 is detached in order to use the syringe.

In the embodiment, the use of the reception seat 9 perfectly prevents rotation and backlash between the holder body 7 and the syringe 1 from occurring. It is a matter of course that the reception seat 9 is not always necessary and the rotation and backlash can be prevented from occurring only by forming the inner face of the engaging member 76 into a shape which allows the basal end flange portion to be fitted into the engaging member.

For example, the rotation and backlash can be prevented from occurring without using the reception seat, in such a manner that the basal end flange portion 22 is formed through a molding into a shape which is not a circle and the inner face of the engaging member 76 is shaped so as to fit with the thus molded basal end flange portion 22.

Figure 6:
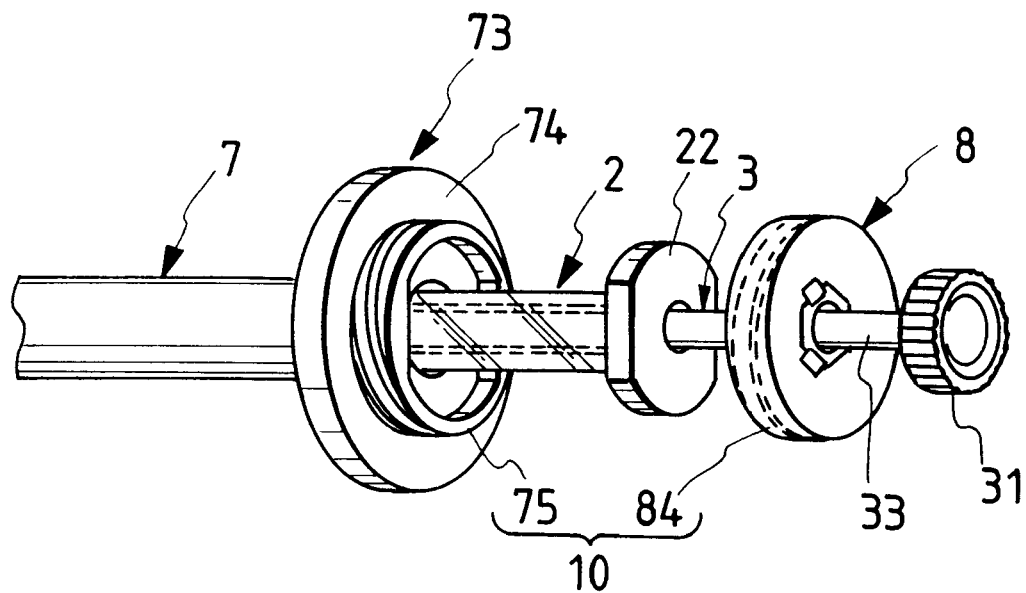
FIG. 6 is an exploded perspective view showing another embodiment of the invention with partial omission.
Figure 7:
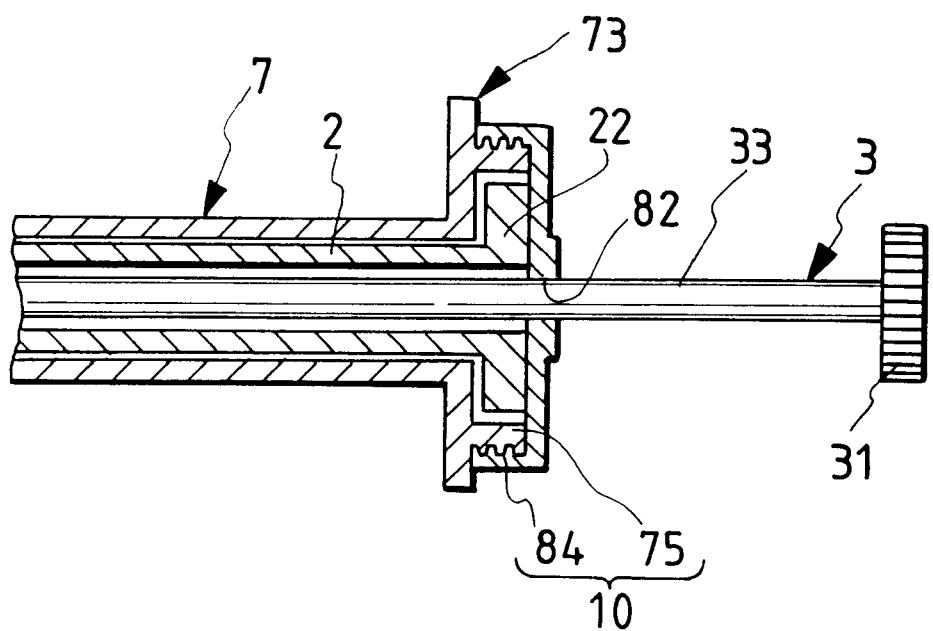
FIG. 7 is a partial longitudinal section view of the embodiment shown in FIG. 6.

FIGS. 6 and 7 show another embodiment of the invention. The embodiment is substantially identical in whole configuration with the above-described embodiment, but different therefrom in that the fixing mechanism 10 between the first engaging ridge 75 of the engaging member 76 formed on the holder body 7 and the second engaging ridge 84 formed on the fixing member 8 is realized by screw fastening.

In the embodiment, therefore, the holder body 7 and the fixing member 8 are fixed to each other so firm so as not to be relatively rotated, so that the fixation of the body and the member is surely conducted. Unlike the above-described embodiment, consequently, the reception seat 9 (see FIG. 2) is not required.

In the above, the embodiments in which the invention is applied to a syringe containing a liquid or gel-like medicine have been described. It is a matter of course that the invention can be applied in the same manner also to a conventional syringe into which liquid or gel is not previously charged. Furthermore, the invention can be applied also to the case where the holder of the invention is applied to a syringe into which a powder is previously charged and a solution liquid for injection is sucked before the use.

As described above, according to the invention, since the holder covers a substantially whole portion of the cylinder barrel of a syringe, the whole of the cylinder barrel has the same diameter which is enlarged. This cooperates with the sure fixation between the holder and the cylinder barrel to enable the syringe to be used under a very stable state. Furthermore, during storage, transportation, and usage, there is no fear that the holder slips off.

An injection needle is lockingly attached to the locking mechanism portion for an injection needle which is formed on the inner side of the tip end of the holder body. This configuration enables the injection needle to be lockingly attached to the holder and syringe even in cases such as that a high pressure is applied to the needle, for example, when liquid or gel of high viscosity is injected under the state of insufficient locking, or when the cylinder barrel is broken.

The configuration in which the reception seat for a finger holding portion (flange) and made of a soft material is disposed on the end face on the basal end side of the flange allows the finger holding portion of the cylinder barrel to be fixed to the flange without producing backlash.

While there has been described in connection with the preferred embodiment of the invention, it will be obvious to those skilled in the art that various changes and modifications may be made therein without departing from the invention, and it is aimed, therefore, to cover in the appended claim all such changes and modifications as fall within the true spirit and scope of the invention.

What is claimed is:

1. A holder for a syringe, said syringe having a piston and a cylinder barrel in which a neck portion for attaching an injection needle is disposed at a tip end of said cylinder barrel and said piston is fittingly inserted into said cylinder barrel through an opening formed at a basal end flange portion thereof, said holder for said syringe comprising:

a body formed into a tubular shape, said holder having a tip end and a basal end, said holder having an inner diameter which allows said holder to be fitted onto an outside of said cylinder barrel of the syringe, and having a length which is substantially equal to a length of said cylinder barrel, and said holder is formed at said basal end thereof with a flange;

wherein said holder has at its basal end a fixing means for preventing said cylinder barrel of said syringe from rotating relative to said flange of said holder.

2. The holder for a syringe according to claim 1, said holder further comprising a locking mechanism portion for lockingly attaching said injection needle to said holder and said syringe is disposed at said tip end of said holder.

3. The holder for a syringe according to claim 2, wherein said locking mechanism portion is constituted by a luer lock mechanism.

4. The holder for a syringe according to claim 1, wherein said fixing means comprises a fixing member disposed under a state where a piston rod of said piston is passed through said fixing member, and said fixing member is fixed to an end face of said flange at said basal end while said basal end flange portion of said cylinder barrel is interposed between said flange and said fixing member.

5. The holder for a syringe according to claim 4, wherein said fixing member prevents backlash between said fixing member and said flange from occurring.

6. The holder for a syringe according to claim 4, wherein said fixing means includes fittingly engaging an engaging portion of said flange with an engaged portion of said fixing member.

7. The holder for a syringe according to claim 4, wherein said fixing means includes threadedly engaging an engaging portion of said flange with an engaged portion of said fixing member.

8. The holder for a syringe according to claim 4, wherein said fixing member fixes said flange portion of said cylinder barrel to said flange of said holder body so as to prevent the syringe from being moved relative to said holder in an axial direction of said syringe.

9. The holder for a syringe according to claim 1, wherein said fixing means has a fitting recess for receiving said basal end flange portion of said cylinder barrel, and said fitting recess is formed in a basal end face of said flange.

10. The holder for a syringe according to claim 1, said cylinder barrel being made of glass, said holder having a tubular shaped holder body made of a hard synthetic resin, and said holder body being provided at said basal end thereof with a flange which is brought in engagement with said flange portion of said cylinder barrel.

11. The holder for a syringe according to claim 1, wherein said fixing means comprises:

a fixing member having a piston rod passed therethrough;
a reception seat made of a relatively soft material as compared to said fixing member for fittingly receiving said basal end flange portion of said cylinder barrel; and
a recessed portion formed in a basal end face of said flange which receives said reception seat.

12. The holder for a syringe according to claim 1, wherein the fixing means comprises a non-circular portion provided at a basal end surface of said flange which is mated with said basal end flange portion of said syringe.

13. An injection device comprising:

a syringe having a piston and a cylinder barrel having a cylinder tip end and a cylinder basal end, and a neck portion disposed at said cylinder tip end, in which said neck portion for attaching an injection needle is disposed at said cylinder tip end of said cylinder barrel and said piston is fittingly inserted into said cylinder barrel through an opening formed at a basal end flange portion disposed at said cylinder basal end thereof, a holder formed into a tubular shape, said holder having a holder tip end and a holder basal end, said holder having an inner diameter which allows said holder to be fitted onto an outside of said cylinder barrel of the syringe, wherein a length of said holder is substantially equal to a length of said cylinder barrel, and said holder is formed at said holder basal end thereof with a flange; and wherein said holder has at its holder basal end a fixing means for preventing said cylinder barrel of said syringe from rotating relative to said flange of said holder.

14. The injection device according to claim 13, said syringe further comprising a cap fitted to said neck portion, and said piston is fittingly inserted in said cylinder barrel to a predetermined distance from said opening in such a manner that a predetermined amount of one of liquid and gel is charged into said cylinder barrel when said piston reaches said predetermined distance from said opening.

15. The injection device according to claim 14, wherein the one of liquid and gel is a liquid medicine of one of high viscosity and a gel-like medicine.

16. The injection device according to claim 14, wherein the one of liquid and gel is a hyaluronic acid preparation.

17. An injection device according to claim 13, said cylinder barrel being made of a glass; and said holder having a tubular shaped holder body made of a hard synthetic resin, and said holder body being provided at said basal end thereof with a flange which is brought in engagement with said flange portion of said cylinder barrel.

18. The injection device according to claim 13, wherein the fixing means comprises a non-circular portion provided at a basal end surface of said flange which is mated with said basal end flange portion of said syringe.

19. The injection device according to claim 13, said holder further comprising a locking mechanism portion for lockingly attaching said injection needle to said holder and said syringe is disposed at said tip end of said holder.

20. The injection device according to claim 19, wherein said locking mechanism portion is constituted by a luer lock mechanism.

21. The injection device according to claim 13, wherein said fixing means comprises a fixing member disposed under a state where a piston rod of said piston is passed through said fixing member, and said fixing member is fixed to an end face of said flange at said basal end while said basal end flange portion of said cylinder barrel is interposed between said flange and said fixing member.

22. The injection device according to claim 21, wherein said fixing member prevents backlash between said fixing member and said flange from occurring.

23. The injection device according to claim 21, wherein said fixing means includes fittingly engaging an engaging portion of said flange with an engaged portion of said fixing member.

24. The injection device according to claim 21, wherein said fixing means includes threadedly engaging an engaging portion of said flange with an engaged portion of said fixing member.

25. The injection device according to claim 21, wherein said fixing member fixes said flange portion of said cylinder barrel to said flange of said holder body so as to prevent the syringe from being moved relative to said holder in an axial direction of said syringe.

26. The injection device according to claim 13, wherein said fixing means has a fitting recess for receiving said basal end flange portion of said cylinder barrel, and said fitting recess is formed in a basal end face of said flange.

27. The injection device according to claim 13, wherein said fixing means comprises:

a fixing member having a piston rod passed therethrough;

a reception seat made of a relatively soft material as compared to said fixing member for fittingly receiving said basal end flange portion of said cylinder barrel; and a recessed portion formed in a basal end face of said flange which receives said reception seat.

* * * * *